US00PP13984P39

(12) United States Plant Patent
Bessho

(10) Patent No.: US PP13,984 P3
(45) Date of Patent: Jul. 15, 2003

(54) PENTUNIA PLANT NAMED 'KAKEGAWA S37'

(75) Inventor: Masao Bessho, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/990,371

(22) Filed: Nov. 23, 2001

(65) Prior Publication Data

US 2003/0101499 P1 May 29, 2003

(51) Int. Cl.[7] ..... A01H 5/00
(52) U.S. Cl. ..... Plt./356

(58) Field of Search ..... Plt./356

(56) References Cited

PUBLICATIONS

UPOV–ROM GTITM Computer Database, 2002/03, GTI Jouve Retrieval Software, citation for 'Kakegawa S37'.*

* cited by examiner

*Primary Examiner*—Bruce R. Campell
*Assistant Examiner*—Susan B. McCormick
(74) *Attorney, Agent, or Firm*—Jondle & Associates PC

(57) ABSTRACT

A Petunia plant particularly distinguished by its lavender pink flower color and creeping, mounding habit.

1 Drawing Sheet

GENUS AND SPECIES

Petunia hybrida.

VARIETY DENOMINATION

'Kakegawa S37'.

BACKGROUND OF THE NEW PLANT

The present invention comprises a new and distinct cultivar of Petunia, botanically known as Petunia hybrida, and hereinafter referred to by the cultivar name 'Kakegawa S37'. 'Kakegawa S37' originated from a hybridization made in 1995 in Kakegawa, Japan. The male parent was a breeding line named P-1a (not patented). The female parent of 'Kakegawa S37' was a dwarf multiflora breeding pool line with red colored flowers named 87S- 1228-1a (not patented). $F_1$ seed from this cross was sown during the summer of 1995 and 20 $F_1$ plants were selected for further evaluation. Three plants were selected for mass intercrossing to produce $F_2$ seed.

One hundred $F_2$ plants were grown to flowering during the spring of 1996. Nine plants were selected for self-pollination. $F_3$ seed from the nine self-pollinated $F_2$ plants was sown during the spring of 1997 and two plants were selected for intercrossing to produce $F_4$ seed. Two hundred plants from this $F_4$ seed were transplanted to the field during the summer of 1998 in Salinas, Calif. One line was selected and vegetatively propagated for further evaluation. This line was propagated again in 1999, and evaluated for fixed characteristics and ease of propagation. The line was established as 'Kakegawa S37', and determined to have its characteristics firmly fixed.

'Kakegawa S37' has been found to retain its distinctive characteristics after two years and four cycles of vegetative propagation and this novelty is firmly fixed. The variety has demonstrated stability during this time and has no inherent variation or off-types.

DESCRIPTION OF PHOTOGRAPH

This new Petunia plant is illustrated by the accompanying photograph which shows blooms, and foliage of the plant in full color, the colors shown being as true as can be reasonably obtained by conventional photographic procedures.

DESCRIPTION OF THE NEW CULTIVAR

Figure 1:
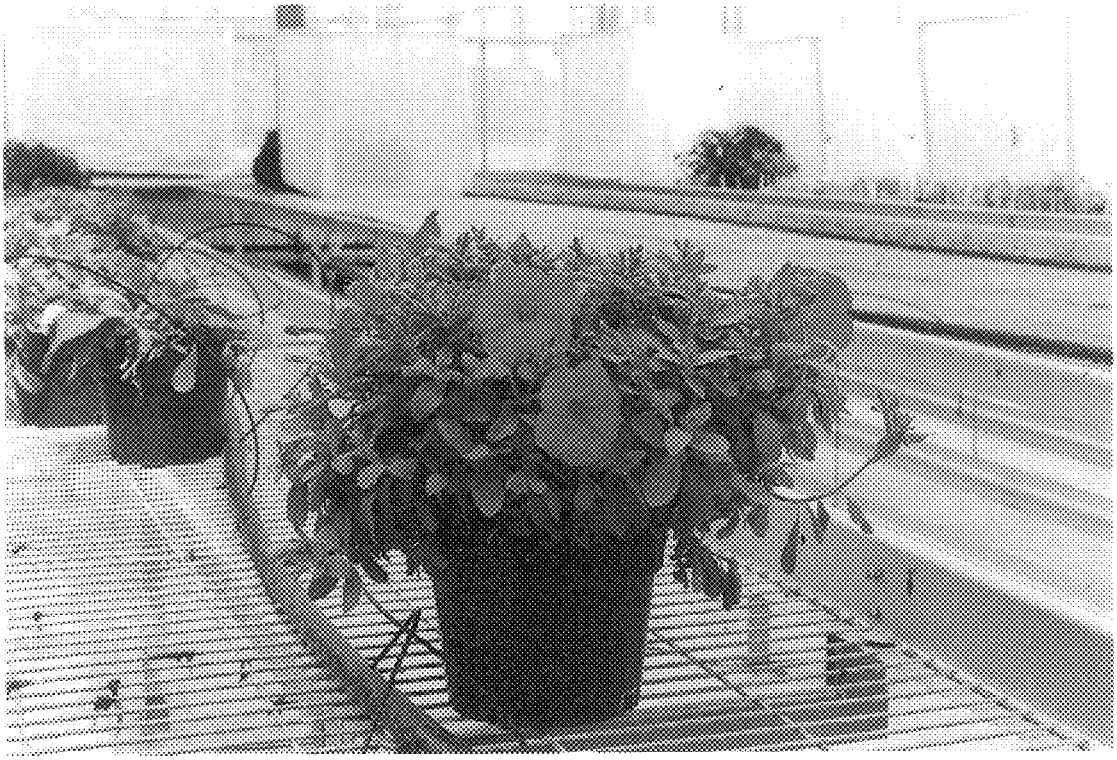
FIG. 1 shows the entire plant approximately eight weeks after transplanting a rooted cutting.
Figure 2:
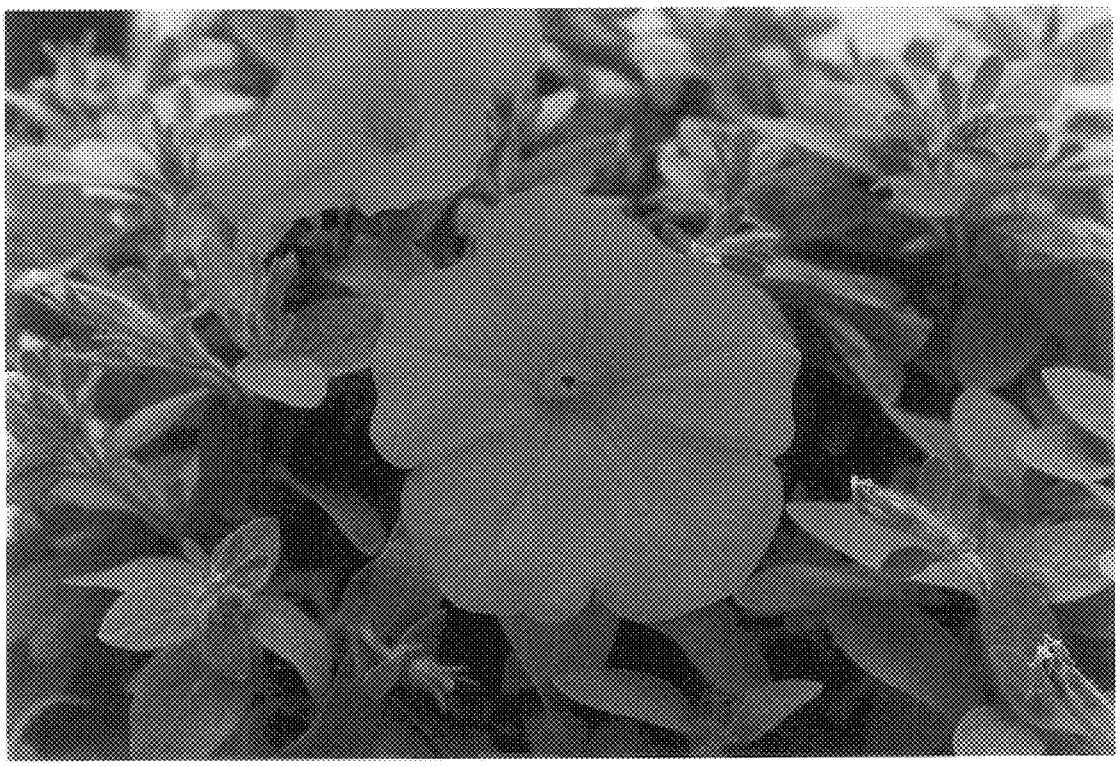
FIG. 2 shows the mature inflorescence.

The following detailed descriptions set forth the distinctive characteristics of 'Kakegawa S37'. The data which defines these characteristics were collected from asexual reproductions carried out in Salinas, Calif. Three plants from fully rooted 15 cm diameter pots were transplanted to one 50 cm diameter hanging baskets and grown in the same conditions. Data was collected on plants in 50 cm diameter pots eight weeks after rooted cuttings were transplanted. Color references are primarily to The R.H.S. Colour Chart of The Royal Horticultural Society of London (R.H.S.).

DESCRIPTION OF THE NEW PLANT

Classification:

*Botanical.*—Petunia hybrida.

*Commerical.*—Petunia.

Parentage:

*Female parent.*—Breeding line 87S-1228-1a (not patented).

*Male parent.*—Breeding line P-1a (not patented).

Environmental conditions for plant growth: Plants were propagated from vegetative cuttings, and grown individually in 15 cm diameter plastic pots in a glass greenhouse located in Salinas, Calif. Pots contained a peat moss-based growing medium. Soluble fertilizer containing 18% nitrogen, 8% phosphorus and 18% potassium was applied in four, daily irrigations. The fifth irrigation was made with non-fertilized water. Pots were top-dressed with a slow release fertilizer containing 18% nitrogen, 8% phosphorus and 18% potassium. The typical average air temperature was 24C.

Growth:

*Habit.*—Branching, mounding.

*Form.*—Descending.

*Plant size.*—45 cm total diameter and 25 cm total height.

*Flowering habit.*—Indeterminate.

*Time to initiate root development.*—7 days after sticking cuttings.

*Time to bloom from propagation.*—4–6 weeks after rooting when grown in 10–15 cm diameter plastic pots.

*Life cycle.*—Annual.

Stems:

*Color.*—Yellow-green (RHS 145A).

*Description.*—Round, pubescent.

*Diameter.*—2–3 mm.

*Internode length.*—3 cm.

Leaves:

*Arrangement.*—Opposite.

*Apex.*—Mucronate.

*Base.*—Oblique.

*Color.*—Upper surface is green (RHS 137B) and lower surface is green (RHS 138B).

*Margin.*—Entire.

*Size.*—Length is 4.8 cm and width is 2.5 cm, both at full expansion.

*Shape.*—Ovate.

*Texture.*—Coarse.

*Venation.*—Pinnate.

*Pubescence.*—Present, clear.

Buds:

*Bud color.*—Yellow-green (RHS 144C).

*Bud diameter.*—5.0 mm.

*Bud length.*—1.8 cm.

Flowers:

*Calyx.*—5 sepals; 2 cm×8 mm (length×width).

*Corolla.*—5 petals, fused.

*Flower diameter.*—5.0–5.5 cm.

*Fragrant.*—Yes.

*Inflorescence type.*—Solitary.

*Pistil.*—Compound.

*Ovary.*—Superior, parietal placentation.

*Stamens.*—5 total with two long and three short; purple (RHS 77D).

*Style.*—Yellow-green (RHS 145C).

*Peduncle.*—2.7 cm×2 mm (length×width); pubescent.

*Petal color.*—Limbs: upper — purple (RHS N78B); lower—purple (RHS N78D) with yellow-green (RHS N144A) veins. Tube: Inner — purple (RHS N78D); Outside is violet (RHS 84C) with yellow-green (RHS N144A) veins.

*Petal margin.*—Smooth.

*Petal pubescence.*—Absent.

*Tube throat diameter.*—0.8 mm.

*Pollen color.*—White (RHS 155C).

*Produces seed.*—Yes; grey-orange (RHS 172B); <1.0 mm diameter; seed coat has netted pattern, 8–10,000 seeds/gram.

Disease and Insect Resistance

No susceptibility to diseases or insects noted to date.

Comparison with Known Cultivars

'Kakegawa S37' is a distinct variety of Petunia owing to its lavender pink flower color and creeping, mounding habit. 'Kakegawa S37' is most similar to the variety 'Pink Wave'; however, 'Kakegawa S37' has a lavender pink flower color. Table 1 below shows the characteristics that best distinguish the new variety from the comparison variety.

TABLE 1

| Characteristic | 'Kakegawa S37' | 'Pink Wave' |
|---|---|---|
| Flower diameter | 5.0–5.5 cm | 8.0–8.5 cm |
| Primary petal color (upper) | Lavender pink RHS N78B | Rosy pink blush RHS 66A |
| Primary petal color (lower) | Lavender pink RHS N78D | White with a rosy pink margin RHS 68B |

Comparison with Parental Cultivars

TABLE 2

| Characteristic | 'Kakegawa S37' | P-1a (male) | 87S-1228-1a (female) |
|---|---|---|---|
| Plant Habit | Mounding | Creeping | Dwarf and compact |
| Flower Size | Grandiflora | Grandiflora | Grandiflora |
| Flower Petal Color | Lavender-pink | Magenta | Red |

I claim:

1. A new and distinct Petunia plant as shown and described herein.

* * * * *